United States Patent [19]

Andree et al.

[11] Patent Number: 5,129,944
[45] Date of Patent: Jul. 14, 1992

[54] HERBICIDAL ARYLOXYNAPHTHALENE DERIVATIVES

[75] Inventors: Roland Andree, Langenfeld; Michael Haug; Klaus Lürssen, both of Bergisch Gladbach; Hans-Joachim Santel, Leverkusen; Robert R. Schmidt, Bergisch Gladbach, all of Fed. Rep. of Germany

[73] Assignee: Bayer Aktiengesellschaft, Leverkusen, Fed. Rep. of Germany

[21] Appl. No.: 569,322

[22] Filed: Aug. 17, 1990

[30] Foreign Application Priority Data

Sep. 1, 1989 [DE] Fed. Rep. of Germany ....... 3928988

[51] Int. Cl.$^5$ .................. A01N 31/00; C07C 323/22; C07C 69/66; C07C 59/72
[52] U.S. Cl. ........................................................ 71/98
[58] Field of Search ............... 560/10, 56; 562/427, 562/466; 71/98, 108, 116

[56] References Cited

U.S. PATENT DOCUMENTS 4,633,008 12/1986 Oonishi et al. .................... 560/15

FOREIGN PATENT DOCUMENTS 0109311 5/1984 European Pat. Off. .
0179015 4/1986 European Pat. Off. .
0309864 4/1989 European Pat. Off. .
358557 9/1980 Fed. Rep. of Germany .

*Primary Examiner*—Jose G. Dees
*Assistant Examiner*—Vera C. Clarke
*Attorney, Agent, or Firm*—Sprung Horn Kramer & Woods

[57] ABSTRACT

A herbicidal aryloxynaphthalene derivatives of the formula

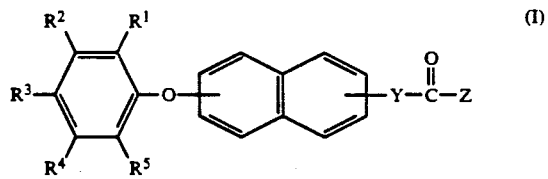

in which
  $R^1$ is selected from the group consisting of hydrogen, halogen, cyano and trifluoromethyl,
  $R^2$ is hydrogen or halogen,
  $R^3$ is selected from the group consisting of halogen, trifluoromethyl, trifluoromethoxy, trifluoromethylthio and trifluoromethylsulphonyl,
  $R^4$ is hydrogen or halogen,
  $R^5$ is alkoxy or alkylthio,
  Y is selected from the group consisting of —A—, —O—A— and —S—A,
  where
    A is an optionally halogen-substituted alkanediyl, and
  Z is selected from the group consisting of hydroxyl, alkoxy, alkenyloxy, alkynyloxy, halogenoalkoxy, alkoxyalkoxy, aralkoxyalkoxy, alkoxycarbonylalkoxy, arylalkoxy, amino, alkylamino, alkenylamino, alkynylamino, dialkylamino, dialkenylamino, dialkynylamino, alkoxyalkylamino and alkoxycarbonylalkylamino.

9 Claims, No Drawings

HERBICIDAL ARYLOXYNAPHTHALENE DERIVATIVES

The invention relates to new aryloxynaphthalene derivatives, to several processes for their preparation, and to their use as herbicides.

It is known that certain aryloxynaphthalene derivatives, such as, for example, ethyl α-(7-(2-chloro-4-trifluoromethyl-phenoxy)-naphthalen-2-yl-oxy)-propionate, have herbicidal properties (cf. EP-A 179,015). However, the action of these known compounds against weeds is not satisfactory in all respects.

New aryloxynaphthalene derivatives of the general formula (I)

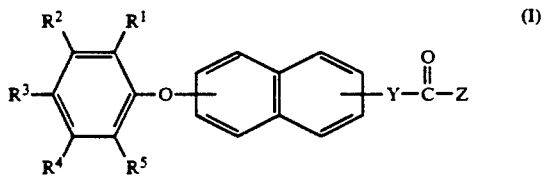

in which
R$^1$ represents hydrogen, halogen, cyano or trifluoromethyl,
R$^2$ represents hydrogen or halogen,
R$^3$ represents halogen, trifluoromethyl, trifluoromethoxy, trifluoromethylthio or trifluoromethylsulphonyl,
R$^4$ represents hydrogen or halogen,
R$^5$ represents alkoxy or alkylthio,
Y represents one of the groups —A—, —O—A— or —S—A—,
where
A represents optionally halogen-substituted alkanediyl, and
Z represents hydroxyl, alkoxy, alkenyloxy, alkynyloxy, halogenoalkoxy, alkoxyalkoxy, aralkoxyalkoxy, alkoxycarbonylalkoxy, arylalkoxy, amino, alkylamino, alkenylamino, alkynylamino, dialkylamino, dialkenylamino, dialkynylamino, alkoxyalkylamino or alkoxycarbonylalkylamino,
have now been found.

In the event that a carbon atom in the radical A is asymmetrical, the invention relates to the mixtures of isomers as well as to the pure R- and S-isomers, preferably to the racemic mixtures and the R-isomers.

It has furthermore been found that the new aryloxynaphthalene derivatives of the general formula (I) are obtained when (a) halogenoaryloxynaphthalene derivatives of the general formula (II)

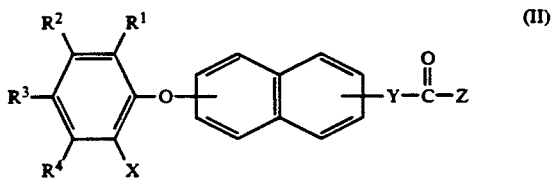

in which
R$^1$, R$^2$, R$^3$, R$^4$, Y and Z have the abovementioned meanings, and
X represents halogen,
are reacted with alkanols or alkanethiols and/or with their alkali metal salts, if appropriate in the presence of an acid acceptor and if appropriate in the presence of a diluent, or when (b) in the event that Y in formula (I) represents one of the groups —O—A— or —S—A— and R$^1$, R$^2$, R$^3$, R$^4$, R$^5$ and Z have the abovementioned meanings, aryloxynaphthalenes of the general formula (III)

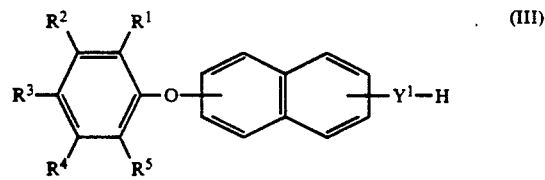

in which
R$^1$, R$^2$, R$^3$, R$^4$ and R$^5$ have the abovementioned meanings, and
Y$^1$ represents oxygen or sulphur,
are reacted with carboxylic acid derivatives of the general formula (IV)

in which
A and Z have the abovementioned meanings, and
X$^1$ represents a nucleophilic leaving group,
if appropriate in the presence of an acid acceptor and if appropriate in the presence of a diluent.

Finally, it has been found that the new aryloxynaphthalene derivatives of the general formula (I) have interesting herbicidal properties.

Surprisingly, the aryloxynaphthalene derivatives of the formula (I) according to the invention have a considerably more powerful herbicidal action than the known compound ethyl α-(7-(2-chloro-4-trifluoromethylphenoxy)-naphthalen-2-yl-oxy)-propionate, which is a previously known active compound of a similar structure and the same direction of action.

The carbon chains in the hydrocarbon groups, such as, for example, alkyl, alkenyl, alkynyl, alkoxy, alkenyloxy, alkynyloxy, alkylamino, alkenylamino, alkynylamino or alkanediyl, are in each case straight-chain or branched.

The invention preferably relates to compounds of the formula (I) in which
R$^1$ represents hydrogen, fluorine, chlorine, bromine, cyano or trifluoromethyl,
R$^2$ represents hydrogen, fluorine or chlorine,
R$^3$ represents fluorine, chlorine, bromine, trifluoromethyl, trifluoromethoxy, trifluoromethylthio or trifluoromethylsulphonyl,
R$^4$ represents hydrogen, fluorine or chlorine,
R$^5$ represents C$_1$-C$_4$-alkoxy or C$_1$-C$_4$-alkylthio,
Y represents one of the groups —A—, —O—A— or —S—A—,
where
A represents C$_1$-C$_4$-alkanediyl which is optionally substituted by fluorine, chlorine and/or bromine, and
Z represents hydroxyl, C$_1$-C$_6$-alkoxy, C$_3$-C$_6$-alkenyloxy, C$_3$-C$_6$-alkynyloxy, C$_1$-C$_6$-halogenoalkoxy, C$_1$-C$_4$-alkoxy-C$_1$-C$_4$-alkoxy, benzyloxy-C$_2$-C$_3$-alkoxy, C$_1$-C$_4$-alkoxycarbonyl- $C_1$–$C_3$-alkoxy, benzyloxy, amino, $C_1$–$C_6$-alkylamino, $C_3$–$C_6$-alkenylamino, $C_3$–$C_6$-alkinylamino, di-($C_3$–$C_4$-alkyl)-amino, Di-($C_3$–$C_4$-alkenyl)-amino, di-($C_3$–$C_4$-alkynyl)-amino, $C_1$–$C_4$-alkoxy-$C_1$–$C_4$-alkylamino or $C_1$–$C_4$-alkoxy-carbonyl-$C_1$–$C_3$-alkylamino.

The invention particularly relates to Compounds of the formula (I) in which
- $R^1$ represents chlorine,
- $R^2$ represents hydrogen,
- $R^3$ represents trifluoromethyl,
- $R^4$ represents hydrogen,
- $R^5$ represents methoxy, ethoxy, propoxy, methylthio or ethylthio,
- Y represents one of the groups —$A^1$—, —O—$A^2$— or —S—$A^2$—
  where
  $A^1$ represents ethane-1,2-diyl which is optionally substituted by chlorine, and
  $A^2$ represents methylene or ethane-1,1-diyl (ethylidene) and
- Z represents hydroxyl, methoxy, ethoxy, propoxy, isopropoxy, butoxy, sec-butoxy, isobutoxy, tert-butoxy, methoxyethoxy, ethoxyethoxy, methoxycarbonylmethoxy, ethoxycarbonylmethoxy, methoxycarbonylethoxy, ethoxycarbonylethoxy, benzyloxy, benzyloxyethoxy, amino, methylamino, ethylamino, propylamino, isopropylamino, butylamino, isobutylamino, sec-butylamino, tert-butylamino, methoxyethylamino, ethoxyethylamino, methoxycarbonylmethylamino, ethoxycarbonylmethylamino, methoxycarbonylethylamino or ethoxycarbonylethylamino.

Very particularly preferred groups of compounds of the formula (I) are those of the formulae (IA) to (IF) below, in which $R^1$, $R^2$, $R^3$, $R^4$, $R^5$, Y and Z in each case have the meanings indicated above as being particularly preferred. The group (IB) may be particularly emphasized.

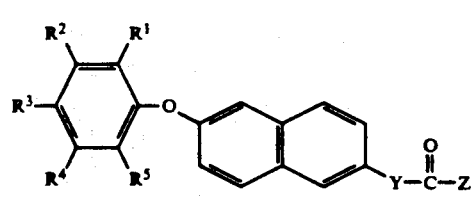
(IA)

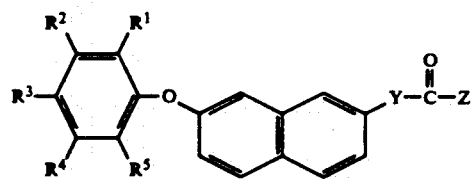
(IB)

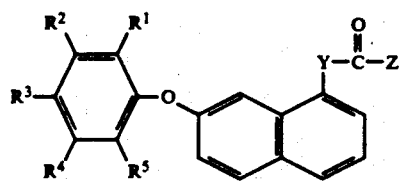
(IC)

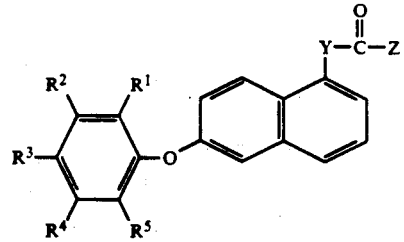
(ID)

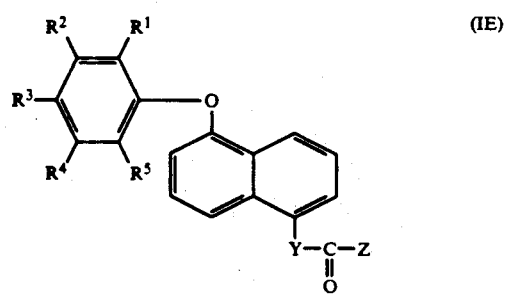
(IE)

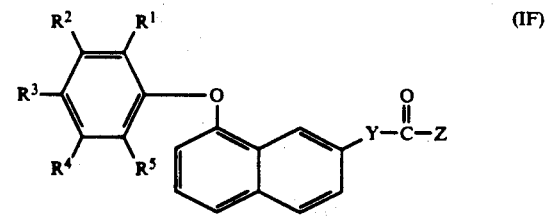
(IF)

The compounds of the formula (I) which are listed in Table 1 below may be mentioned as examples:

TABLE 1

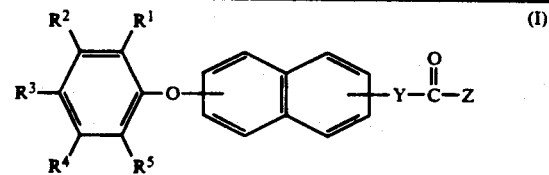
(I)

| $R^1$ | $R^2$ | $R^3$ | $R^4$ | $R^5$ | Y | Z |
|---|---|---|---|---|---|---|
| Cl | H | $CF_3$ | H | $OCH_3$ | —O—$CH_2$— | OH |
| Cl | H | $CF_3$ | H | $OCH_3$ | —O—$CH_2$— | $OCH_3$ |
| Cl | H | $CF_3$ | H | $OCH_3$ | —O—$CH_2$— | $OC_2H_5$ |
| Cl | H | $CF_3$ | H | $OC_2H_5$ | —O—$CH_2$— | OH |
| Cl | H | $CF_3$ | H | $OC_2H_5$ | —O—$CH_2$— | $OCH_3$ |
| Cl | H | $CF_3$ | H | $OC_2H_5$ | —O—$CH_2$— | $OC_2H_5$ |
| Cl | H | $CF_3$ | H | $OCH_3$ | —O—CH(—$CH_3$)— | OH |
| Cl | H | $CF_3$ | H | $OCH_3$ | —O—CH(—$CH_3$)— | $OCH_3$ |
| Cl | H | $CF_3$ | H | $OCH_3$ | —O—$CH_2$— | $OC_4H_9$ |
| Cl | H | $CF_3$ | H | $OCH_3$ | —S—$CH_2$— | OH |
| Cl | H | $CF_3$ | H | $OCH_3$ | —S—$CH_2$— | $OCH_3$ |
| Cl | H | $CF_3$ | H | $OCH_3$ | —S—CH(—$CH_3$)— | $OCH_3$ |
| Cl | H | $CF_3$ | H | $OC_2H_5$ | —S—$CH_2$— | $OC_2H_5$ |
| Cl | H | $CF_3$ | H | $OCH_3$ | —S—CH(—$CH_3$)— | OH |

TABLE 1-continued

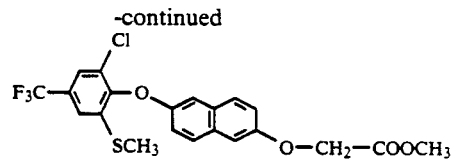

| $R^1$ | $R^2$ | $R^3$ | $R^4$ | $R^5$ | Y | Z |
|---|---|---|---|---|---|---|
| Cl | H | $CF_3$ | H | $SCH_3$ | $-O-CH_2-$ | OH |
| Cl | H | $CF_3$ | H | $SCH_3$ | $-O-CH_2-$ | $OCH_3$ |
| Cl | H | $CF_3$ | H | $SCH_3$ | $-O-CH_2-$ | $OCH(CH_3)_2$ |
| Cl | H | $CF_3$ | H | $SCH_3$ | $-S-CH_2-$ | OH |
| Cl | H | $CF_3$ | H | $SCH_3$ | $-S-CH(CH_3)-$ | $OCH_3$ |
| Cl | H | $CF_3$ | H | $OCH_3$ | $-CH_2CH_2-$ | OH |
| Cl | H | $CF_3$ | H | $OCH_3$ | $-CH_2CH_2-$ | $OCH_3$ |
| Cl | H | $CF_3$ | H | $OCH_3$ | $-CH_2-CH(Cl)-$ | $OCH_3$ |

The examples indicated in Table 1 specifically apply to the groups of compounds of the formula (I) which are outlined by the formulae (IA) to (IF).

If, for example, ethyl α-(7-(2,6-dichloro-4-trifluoromethyl-phenoxy)-naphthalen-2-yl-oxy)-propionate and sodium methylate are used as starting substances for process (a) according to the invention, the course of the reaction can be represented by the following equation:

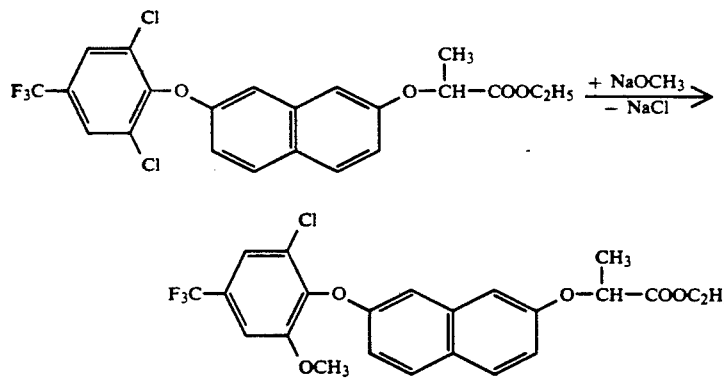

If, for example, 6-(2-chloro-6-methylthio-4-trifluoromethyl-phenoxy)-2-naphthol and methyl bromoacetate are used as starting substances in process (b) according to the invention, the course of the reaction can be represented by the following equation:

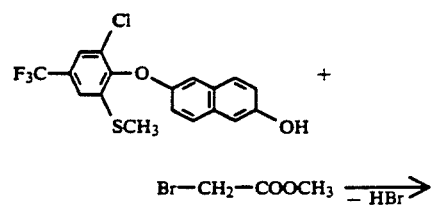

Formula (II) provides a general definition of the halogenoaryloxynaphthalene derivatives to used as starting substances in process (a) according to the invention for the preparation of compounds of the formula (I).

In formula (II), $R^1$, $R^2$, $R^3$, $R^4$, Y and Z preferably, or in particular, have those meanings which have already been mentioned above in connection with the description of the compounds of the formula (I) according to the invention as being preferred, or particularly preferred, for $R^1$, $R^2$, $R^3$, $R^4$, Y and Z, and X preferably represents fluorine, chlorine or bromine, in particular chlorine or fluorine.

Starting substances of the formula (II) are known and/or the subject of previous Patent Applications (cf. EP-A 179,015, EP-A 308,755, EP-A 309,864, EP-A 315,008, DE-P (German Patent) 3,823,318 dated Jul. 9, 1988, DE-P (German Patent) 3,821,389 dated Jun. 24, 1988 or DE-P (German Patent) 3,837,464 dated Nov. 4, 1988).

The non-prior-published starting substances of the formula (II) in which Y represents the group —S—A— and $R^1$, $R^2$, $R^3$, $R^4$, A, X and Z have the abovementioned meanings (cf. also DE-P (German Patent) 3,823,318 dated Jul. 9, 1988) are obtained for example when, in a first step, halogenobenzene derivatives of the general formula (V)

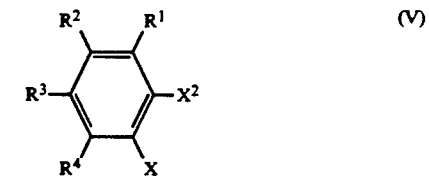

in which $R^1$, $R^2$, $R^3$, $R^4$ and X have the abovementioned meanings, and $X^2$ represents halogen, preferably fluorine or chlorine, are reacted with hydroxynaphthalenesulphonic acids of the general formula (VI)

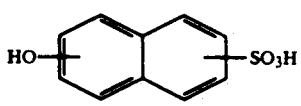

or with their metal salts, if appropriate in the presence of acid acceptors, such as, for example, sodium hydroxide or potassium hydroxide, and if appropriate in the presence of diluents, such as, for example, dimethylformamide or dimethyl sulphoxide, at temperatures between 20° C. and 120° C. In a second step, the resulting aryloxynaphthalenesulphonic acid derivatives of the general formula (VII)

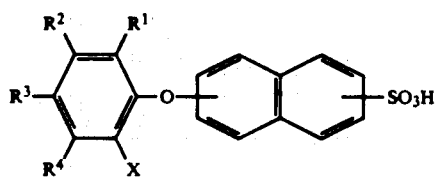

in which
R¹, R², R³, R⁴ and X have the abovementioned meanings, or metal salts thereof,
are reacted with halogenating agents, such as, for example, phosphorus(V) chloride and/or phosphoryl chloride (phosphorus oxychloride), at temperatures between 0° C. and 100° C. In a third step, the resulting aryloxynaphthalenesulphonyl chlorides of the general formula (VIII)

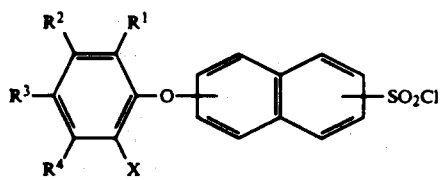

in which
R¹, R², R³, R⁴ and X have the abovementioned meanings, are reacted with reducing agents, such as, for example, zinc dust, if appropriate in the presence of reducing auxiliaries, such as, for example, hydrochloric acid or acetic acid, and if appropriate in the presence of a diluent, such as, for example, dioxane, at temperatures between 10° C. and 120° C. In a fourth step, the resulting aryloxynaphthalenethiols of the general formula (IXa)

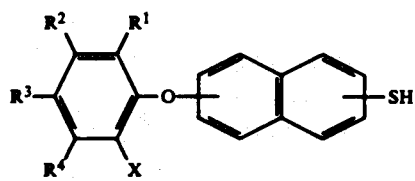

in which
R¹, R², R³, R⁴ and X have the abovementioned meanings, are reacted with carboxylic acid derivatives of the general formula (IV)

in which
A, X¹ and Z have the abovementioned meanings, if appropriate in the presence of an acid acceptor, such as, for example, potassium carbonate, and if appropriate in the presence of a diluent, such as, for example acetonitrile, at temperatures between 0° C. and 80° C. (cf. also the Preparation Examples).

The starting substances required, of the formulae (IV), (V) and (VI), are known organic intermediates.

Process (a) according to the invention is carried out using alkanols or alkanethiols, or their alkali metal salts. It is preferred to employ alkanols or alkanethiols having in each case 1 to 4 carbon atoms, in particular 1 or 2 carbon atoms, or their sodium or potassium salts.

Process (a) according to the invention for the preparation of the new compounds of the formula (I) is preferably carried out using diluents. Diluents which are suitable for this purpose are virtually all inert organic solvents. These preferably include aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methyl-pyrrolidone, and also dimethyl sulphoxide, tetramethylene sulphone and hexamethylphosphoric triamide.

Diluents which can also be used in process (a) according to the invention are alcohols, such as, for example, methanol, ethanol, propanol, isopropanol, butanol, isobutanol, sec-butanol and tert-butanol.

Acid acceptors which can be employed in process (a) according to the invention are all acid-binding agents which can customarily be used for reactions of this type. The following are preferably suitable: alkali metal hydroxides, such as, for example, sodium hydroxide and potassium hydroxide, alkaline earth metal hydroxides, such as, for example, calcium hydroxide, alkali metal carbonates and alkali metal alcoholates, such as sodium carbonate, potassium carbonate, sodium tert-butylate and potassium tert-butylate, furthermore aliphatic, aromatic or heterocyclic amines, for example triethylamine, trimethylamine, dimethylaniline, dimethylbenzylamine, pyridine, 1,5-diazabicyclo-[4,3,0]-non-5-ene (DBN), 1,8-diazabicyclo-[5,4,0]-undec-7-ene (DBU) and 1,4-diazabicyclo-[2,2,2]-octane (DABCO).

In process (a) according to the invention, the reaction temperatures can vary within a substantial range. In general, the process is carried out at temperatures between 0° C. and 150° C., preferably at temperatures between 20° C. and 120° C.

Process (a) according to the invention is generally carried out at atmospheric pressure. However, it is also possible to carry out the process under increased or reduced pressure.

For carrying out process (a) according to the invention, between 1 and 1,000 moles of an alkanol or alkanethiol and/or their alkali metal salts is generally employed per mole of halogenoaryloxynaphthalene derivative of the formula (II).

It is preferred to employ between 1.5 and 5 moles of an alkali metal salt of an alkanol or alkanethiol and additionally between 50 and 500 moles of an alcohol per mole of starting compound of the formula (II).

In general, the reactants are mixed at room temperatures, and the reaction mixture is stirred at an increased temperature until the reaction is complete. The mixture can be worked up by customary methods.

Formula (III) provides a general definition of the aryloxynaphthalenes to be used as starting substances in process (b) according to the invention for the preparation of compounds of the formula (I).

In formula (III), $R^1$, $R^2$, $R^3$, $R^4$ and $R^5$ preferably, or in particular, have those meanings which have already been mentioned above in connection with the description of the compounds of the formula (I) according to the invention as being preferred, or particularly preferred, for $R^1$, $R^2$, $R^3$, $R^4$ and $R^5$, and $Y^1$ represents oxygen or sulphur.

The starting substances of the formula (III) were hitherto unknown from the literature. The new aryloxynaphthalenes of the formula (III) are obtained when halogenoaryloxynaphthalenes of the general formula (IX)

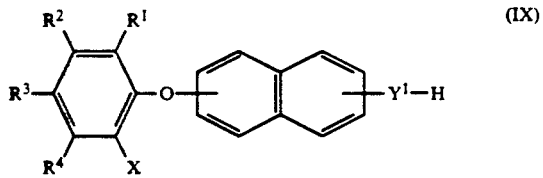

in which
$R^1$, $R^2$, $R^3$, $R^4$, X and $Y^1$ have the abovementioned meanings, are reacted with alkanols or alkanethiols, such as, for example, methanol, ethanol, methanethiol or ethanethiol, and/or their alkali metal salts, preferably their sodium or potassium salts, at temperatures between 20° C. and 120° C. (cf. the Preparation Examples).

In formula (IX), $R^1$, $R^2$, $R^3$, $R^4$, X and $Y^1$ preferably, or in particular, have those meanings which have already been mentioned above in connection with the description of the compounds of the formulae (I), (II) and (III) according to the invention as being preferred, or particularly preferred, for $R^1$, $R^2$, $R^3$, $R^4$, X and $Y^1$.

The compounds of the formula (IX) are known and/or the subject of previous Patent Applications (cf. EP-A 179,015, EP-A 308,755, EP-A 309,864, EP-A 315,008, DE-P (German Patent) 3,823,318 dated Jul. 9, 1988 or DE-P (German Patent) 3,821,389 dated Jun. 24, 1988).

Formula (IV) provides a general definition of the carboxylic acid derivatives furthermore to used as starting substances in process (b) according to the invention. In formula (IV), A and Z preferably, or in particular, have those meanings which have already been mentioned above within the scope of the description of the compounds of the formula (I) according to the invention as being preferred, or particularly preferred, for A and Z, and $X^1$ preferably represents chlorine, bromine, iodine, optionally fluorine- or chlorine-substituted $C_1$-$C_4$-alkylsulphonyloxy or optionally fluorine-, chlorine-, bromine- or methyl-substituted phenylsulphonyloxy, in particular chlorine, bromine, methylsulphonyloxy, phenylsulphonyloxy or 4-methyl-phenylsulphonyloxy.

The starting substances of the formula (IV) are known and/or can be prepared by processes known per se (cf. DE-OS (German Published Specification) 2,758,002 and DE-OS (German Published Specification) 2,854,542).

Process (b) according to the invention is preferably carried out in the presence of a diluent. Diluents which are suitable for this purpose are those which have been indicated above for process (a) according to the invention.

Process (b) is preferably carried out in the presence of an acid acceptor. Suitable acid acceptors are the same as have been indicated above for process (a) according to the invention.

In process (b) according to the invention, the reaction temperatures can be varied within a substantial range. In general, the process is carried out at temperatures between 0° C. and 150° C., preferably at temperatures between 10° C. and 120° C.

Process (b) according to the invention is generally carried out under atmospheric pressure. However, it is also possible to carry out the process under increased or reduced pressure.

For carrying out process (b) according to the invention, the specifically required starting substances are generally employed in approximately equimolar amounts. However, it is also possible to use one of the two specifically employed components in a substantial excess. In general, the reactions are carried out in a suitable diluent in the presence of an acid acceptor, and the reaction mixture is stirred for several hours at the specifically required temperature. Working up in process (b) according to the invention is carried out in each case by customary methods.

The active compounds according to the invention can be used as defoliants, desiccants, agents for destroying broad-leaved plants and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The compounds of the formula (I) according to the invention are suitable for selectively combating weeds both of monocotyledon and dicotyledon weeds in monocotyledon and dicotyledon crops, both by the pre-emergence and post-emergence method.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N'-dimethylurea (METABENZTHIAZURON) for combating weeds in cereals; 4-amino-3-methyl-6-phenyl-1,2,4-triazin-5(4H)-one (METAMITRON) for combating weeds in sugar beets and 4-amino-6-(1,1-dimethylethyl)-3-methylthio-1,2,4-triazin-5(4H)-one (METRIBUZIN) for combating weeds in soy beans; furthermore also 2,4-dichlorophenoxyacetic acid (2,4-D); 4-(2,4-dichlorophenoxy)-butyric acid (2,4-DB); 2,4-dichlorophenoxypropionic acid (2,4-DP); 5-(2-chloro-4-trifluoromethyl-phenoxy)-2-nitro-benzoic acid (ACIFLUORFEN); 2-chloro-2',6'-diethyl-N-methoxymethylacetanilide (ALACHLOR); methyl-6,6-dimethyl-2,4-dioxo-3-[1-(2-propenyloxyamino)-butylidene]-cyclohexanecarboxylic acid (ALLOXYDIM); 2-chloro-4-ethylamino-6-isopropylamino-1,3,5-triazine (ATRAZINE); 3-isopropyl-2,1,3-benzothiadiazin-4-one 2,2-dioxide (BENTAZONE); methyl 5-(2,4-dichlorophenoxy)-2-nitrobenzoate (BIFENOX); 3,5-dibromo-4-hydroxy-benzonitrile (BROMOXYNIL); ethyl 2-{[(4-chloro-6-methoxy-2-pyrimidinyl)-aminocarbonyl]-aminosulphonyl}-benzoate (CHLORIMURON); 2-chloro-N-{[(4-methoxy-6-methyl-1,3,5-triazin-2-yl)-amino]-carbonyl}-benzenesulphonamide (CHLORSULFURON); N,N-dimethyl-N'-(3-chloro-4-methylphenyl)-urea (CHLORTOLURON); exo-1-methyl-4-(1-methylethyl)-2-(2-methylphenyl-methoxy)-7-oxabicyclo-(2,2,1)-heptane (CINMETHYLIN); 3,6-dichloro-2-pyridinecarboxylic acid (CLOPYRALID); 2-chloro-4-ethylamino-6-(3-cyanopropylamino)-1,3,5-triazine (CYANAZINE); 2-[4-(2,4-dichlorophenoxy)-phenoxy]-propionic acid, its methyl ester or its ethyl ester (DICLOFOP); 2-[(2-chlorophenyl)-methyl]-4,4-dimethylisoxazolidin-3-one (DIMETHAZONE); 4-amino-6-t-butyl-3-ethylthio-1,2,4-triazin-5(4H)-one (ETHIOZIN); 2-{4-[(6-chloro-2-benzoxazolyl)-oxy]-phenoxy}-propanoic acid, its methyl ester or its ethyl ester (FENOXAPROP); 2-[4-(5-trifluoromethyl-2-pyridyloxy)-phenoxy]-propanoic acid or its butyl ester (FLUAZIFOP); [(4-amino-3,5-dichloro-6-fluoro-2-pyridinyl)-oxy]-acetic acid or its 1-ethylheptyl ester (FLUROXYPYR); 5-(2-chloro-4-trifluoromethylphenoxy)-N-methylsulphonyl-2-nitrobenzamide (FOMESAFEN); 2-{4-[(3-chloro-5-(trifluoromethyl)-2-pyridinyl)-oxy]-phenoxy}-propanoic acid or its ethyl ester (HALOXYFOP);3-cyclohexyl-6-dimethylamino-1-methyl-1,3,5-triazine 2,4-dione (HEXAZINONE); methyl 2-[4,5-dihydro-4-methyl-4-(1-methylethyl)-5-oxo-1H-imidazol-2-yl]-4(5)-methylbenzoate (IMAZAMETHABENZ); 2-[5-methyl-5-(1-methylethyl)-4-oxo-2-imidazolin-2-yl]-3-quinolinecarboxylic acid (IMAZAQUIN); 2-[4,5-dihydro-4-methyl-4-isopropyl-5-oxo-(1H)-imidazol-2-yl]-5-ethylpyridine-3-carboxylic acid (IMAZETHAPYR); 3,5-diiodo-4-hydroxybenzonitrile (IOXYNIL); N,N-dimethyl-N'-(4-isopropylphenyl)-urea (ISOPROTURON); (2-ethoxy-1-methyl-2-oxo-ethyl 5-[2-chloro-4-(trifluoromethyl)-phenoxy]-2-nitrobenzoate (LACTOFEN); (2-methyl-4-chlorophenoxy)-acetic acid (MCPA); (4-chloro-2-methylphenoxy)-propionic acid (MCPP); N-methyl-2-(1,3-benzothiazol-2-yloxy)-acetanilide (MEFENACET); 2-ethyl-6-methyl-N-(1-methyl-2-methoxyethyl)-chloroacetanilide (METOLACHLOR); 2-{[[((4-methoxy-6-methyl-1,3,5-triazin-2-yl)-amino)-carbonyl]-amino]-sulphonyl}-benzoic acid or its methyl ester (METSULFURON); 1-(3-trifluoromethyl-phenyl)-4-methylamino-5-chloro-6-pyridazone (NORFLURAZON); 4-(di-n-propylamino)-3,5-dinitrobenzenesulphonamide (ORYZALIN); 2-chloro-4-trifluoromethylphenyl 3-ethoxy-4-nitro-phenyl ether (OXYFLUORFEN); N-(1-ethylpropyl)-3,4-dimethyl-2,6-dinitroaniline (PENDIMETHALIN); O-(6-chloro-3-phenylpyridazin-4-yl) S-octyl thiocarbonate (PYRIDATE); ethyl 2-[4-(6-chloro-quinoxalin-2-yl-oxy)-phenoxy]-propionate (QUIZALOFOP-ETHYL); 2-[1-(ethoxamino)-butylidene]-5-(2-ethylthiopropyl)-1,3-cyclohexadione (SETHOXYDIM); 2-chloro-4,6-bis-(ethylamino)-1,3,5-triazine (SIMAZINE); 2,4-bis-[N-ethylamino]-6-methylthio-1,3,5-triazine (SIMETRYNE); 4-ethylamino-2-t-butylamino-6-methylthio-s-triazine (TERBUTRYNE); methyl 3-[[[[(4-methoxy-6-methyl-1,3,5-triazin-2-yl)-amino]-carbonyl]-amino]-sulphonyl]-thiophene-2-carboxylate (THIAMETURON); S-(2,3,3-trichloroallyl) diisopropylthiocarbamate (TRIALLATE) and 2,6-dinitro-4-trifluoromethyl-N,N-dipropylaniline (TRIFLURALIN). Surprisingly, some mixtures also show a synergistic action.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the nature of the desired effect. In general, the amounts used are between 5 g and 5,000 g of active compound per hectare of soil surface, preferably between 10 g and 2,000 g per ha.

The preparation and use of the active compounds according to the invention can be seen from the following examples.

PREPARATION EXAMPLES

Example 1

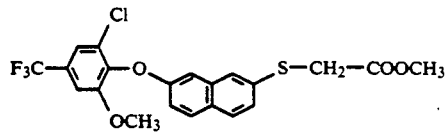

(Process (a))

A mixture of 8.9 g (0.02 mol) of methyl α-(7-(2-chloro-6-fluoro-4-trifluoromethyl-phenoxy)-naphthalen-2-yl-thio)-acetate, 2.7 g (0.05 mol) of sodium methylate and 200 ml of methanol is refluxed for 4 days and then concentrated. The residue is shaken with water-/ethyl acetate, and the organic phase is dried with sodium sulphate and filtered. The filtrate is concentrated, and the residue is purified by column chromatography (silica gel, toluene).

This gives 3.1 g (34% of theory) of methyl α-(7-(2-chloro-6-methoxy-4-trifluoromethyl-phenoxy)-naphthalen-2-yl-thio)-acetate of melting point 115° C.

Example 2

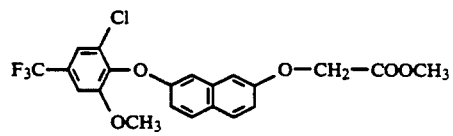

(Process (b))

A mixture of 1.5 g (4 mmol) of 7-(2-chloro-6-methoxy-4-trifluoromethyl-phenoxy)-2-naphthol, 0.6 g (4 mmol) of methyl bromoacetate, 0.6 g of potassium carbonate and 50 ml of acetonitrile is refluxed for 20 hours and then concentrated. The residue is shaken with 2N hydrochloric acid/toluene, and the organic phase is dried with sodium sulphate and filtered. The solvent is carefully removed from the filtrate by distillation in a water pump vacuum.

This gives 1.8 g (97% of theory) of methyl α-(7-(2-chloro-6-methoxy-4-trifluoromethyl-phenoxy)-naphthalen-2-yl-oxy)-acetate as an amorphous residue.

$^1$H NMR (CDCl$_3$, δ, ppm): 3.80 and 3.81 (OCH$_3$ and COOCH$_3$), 4.70 (CH$_2$).

The following are obtained analogously:

Example 3

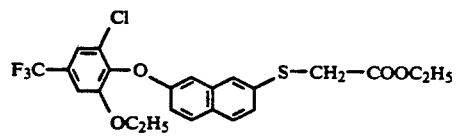

ethyl α-(7-(2-chloro-6-ethoxy-4-trifluoromethyl-phenoxy)-naphthalen-2-yl-thio)-acetate; melting point: 86° C.

Example 4

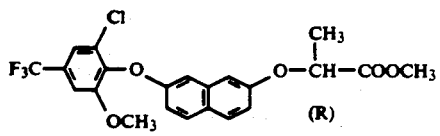

methyl (R)-α-(7-(2-chloro-6-methoxy-4-trifluoromethylphenoxy)-naphthalen-2-yl-oxy)-propionate.

$^1$H NMR (CDCl$_3$, δ, ppm): 3.75 and 3.82 (OCH$_3$ and COOCH$_3$).

STARTING SUBSTANCES OF THE FORMULA (III)

Example (III-1)

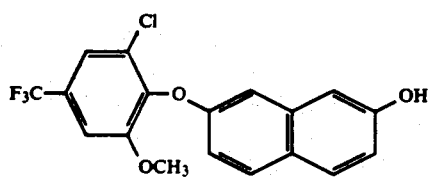

A mixture of 10.7 g (0.03 mol) of 7-(2-chloro-6-fluoro-4-trifluoromethyl-phenoxy)-2-naphthol, 6.4 g (0.12 mol) of sodium methylate and 150 ml of methanol is refluxed for 7 days and then concentrated. The residue is taken up in chloroform, and the mixture is washed with 1N hydrochloric acid and with water, dried with sodium sulphate and filtered. The filtrate is concentrated, the residue is triturated with hexane, and the product which is obtained in crystalline form in this process is isolated by filtration with suction.

This gives 5.1 g (46% of theory) of 7-(2-chloro-6-methoxy-4-trifluoromethyl--phenoxy)-2-naphthol of melting point 130° C.

STARTING SUBSTANCES OF THE FORMULA (II)

Example (II-1)

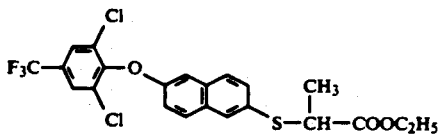

Step 1 (VII-1):

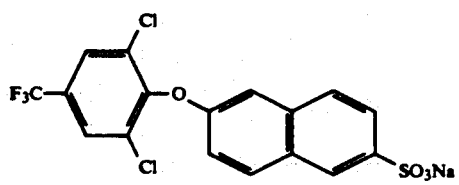

124 g (0.5 mol) of 3,4,5-trichlorobenzotrifluoride are added to a stirred mixture of 135 g (0.5 mol) of the sodium salt of 6-hydroxy-naphthalene-2-sulphonic acid, 30 g (0.54 mol) of potassium hydroxide powder and 1,000 ml of dimethyl sulphoxide, and the reaction mixture is stirred first for 3 hours at 60° C. and then for 15 hours at 20° C. After the mixture has been concentrated, the residue is digested with water, and the product which has been obtained in crystalline form is isolated by filtration with suction. This gives 209.5 g (91% of theory) of the sodium salt of 6-(2,6-dichloro-4-trifluoromethyl-phenoxy)-naphthalene-2-sulphonic acid, which melts above 310° C. with decomposition.

Step 2 (VIII-1)

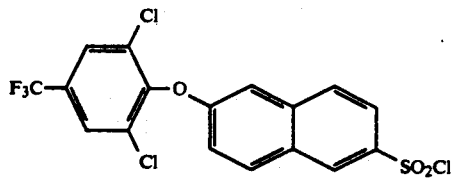

A mixture of 2.3 g (5.0 mmol) of the sodium salt of 6-(2,6-dichloro-4-trifluoromethyl-phenoxy)-naphthalene-2-sulphonic acid, 1.6 g (7.5 mmol) of phosphorus(V) chloride and 15 ml of phosphoryl chloride is first stirred for 6 hours at 70° C. and then for 15 hours at 20° C., subsequently poured into water and stirred for one further hour. The product which is obtained in crystalline form is isolated by filtration with suction.

This gives 1.8 g (79% of theory) of 6-(2,6-dichloro-4-trifluoromethyl-phenoxy)-naphthalene-2-sulphonyl chloride of melting point 140° C.

Step 3 (IXa-1)

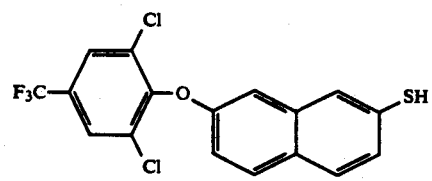

12.5 g (0.025 mol) of 7-(2,6-dichloro-4-trifluoromethyl-phenoxy)-naphthalene-2-sulphonyl chloride and 25 ml of concentrated hydrochloric acid are added in succession to a stirred mixture of 12.5 g (0.19 mol) of zinc dust and 100 ml of dioxane. The reaction mixture is refluxed at boiling point for 5 hours and is then stirred for 15 more hours at 20° C. After the mixture has been concentrated, the residue is taken up in methylene chloride/water and filtered, the filtrate is shaken, and the organic phase is separated off, washed with water, dried with sodium sulphate and filtered.

The filtrate is concentrated, the residue is taken up in ethanol, and the product which is obtained in crystalline form during this process is isolated by filtration with suction.

This gives 4.8 g (49% of theory) of 7-(2,6-dichloro-4-trifluoromethyl-phenoxy)-naphthalene-2-thiol of melting point 98° C.

Step 4 (II-1)

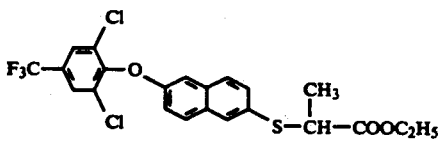

A mixture of 1.9 g (5 mmol) of 6-(2,6-dichloro-4-trifluoromethyl-phenoxy)-naphthalene-2-thiol, 1.0 g (5.5 mmol) of ethyl α-bromo-propionate, 0.7 g (5.5 mmol) of potassium carbonate and 50 ml of acetonitrile is refluxed at boiling point for 15 hours and then concentrated. The residue is taken up in methylene chloride, and the mixture is washed twice with water, dried with sodium sulphate and filtered. The solvent is carefully removed from the filtrate by distillation at 1 torr (0.13 kPa).

This gives 1.4 g (57% of theory) of ethyl α-[6-(2,6-dichloro-4-trifluoromethyl-phenoxy)-naphthalen-2-yl-thio]-propionate as an oily residue.

¹NMR (CDCl₃, δ): 3.8 ppm

USE EXAMPLES

In the following Use Examples, compound (A) listed below is used as comparison substance:

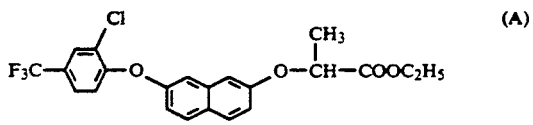

ethyl α-(7-(2-chloro-4-trifluoromethyl-phenoxy)-naphthalen-2-yl-oxy)-propionate (disclosed in EP-A 179,015).

Example A

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added, and the concentrate is diluted with water to the desired concentration.

Test plants of a height of 5–15 cm are sprayed with the preparation of active compound in such a way that the specifically desired amounts of active compound are applied per unit area. The concentration of the spray liquor is chosen such that the specifically desired amounts of active compound are applied in 1,000 l of water/ha. After three weeks, the degree of damage to the plants is rated in % damage in comparison to the development of the untreated control. The figures denote:

0% = no action (like untreated control)
100% = total destruction

In this test, a clearly superior herbicidal activity compared with comparison substance (A) is shown, for example, by the compounds of Preparation Examples 1, 2 and 4.

Example B

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, a powerful action against weeds combined with good tolerance by wheat is shown, for example, by the compounds of Preparation Examples 1 and 4.

It will be understood that the specification and examples are illustrative but not limitative of the present invention and that other embodiments within the spirit and scope of the invention will suggest themselves to those skilled in the art.

We claim:

1. An aryloxynaphthalene of the formula

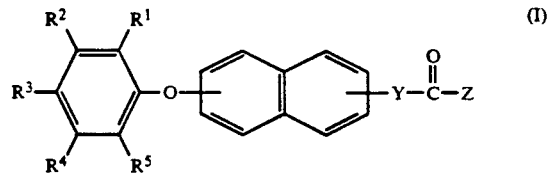

in which
R¹ is chlorine or fluorine,
R² is hydrogen,
R³ is trifluoromethyl or chlorine,
R⁴ is hydrogen,
R⁵ is selected from the group consisting of methoxy, ethoxy, propoxy, methylthio and ethylthio,
Y is selected from the group consisting of —A¹—, —O—A²— and —S—A²—
where
A¹ is ethane-1,2-diyl which can be substituted by chorine, and
A² is methylene or ethane-1,1-diyl and
Z is selected from the group consisting of hydroxyl, methoxy, ethoxy, propoxy, isopropoxy, butoxy, sec-butoxy, isobutoxy, tertbutoxy, methoxyethoxy, ethoxyethoxy and benzyloxy.

2. An aryloxynapthalene according to claim 1 of the formula (IB)

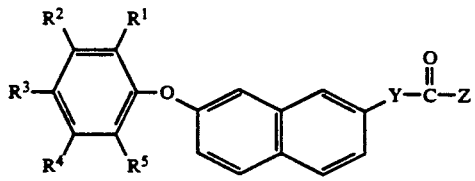

wherein
R¹ represents chlorine or fluorine,
R² represents hydrogen,
R³ represents trifluoromethyl or chlorine,
R⁴ represents hydrogen,
R⁵ represents methoxy, ethoxy, propoxy, methylthio and ethylthio,
Y represents one of the groups —A¹—, —O—A²— and —S—A²—
where A¹ represents ethane-1,2-diyl which can be substituted by chlorine, and A² represents methylene or ethane-1,1-diyl and Z represents hydroxyl, methoxy, ethoxy, propoxy, isopropoxy, butoxy, sec-butoxy, isobutoxy, tert-butoxy, methoxyethoxy, ethoxyethoxy and benzyloxy.

3. A compound according to claim 1, wherein such compound is methyl α-(7-(2-chloro-6-methoxy-4-trifluoromethyl-phenoxy)-naphthalen-2-yl-thio)-acetate of the formula

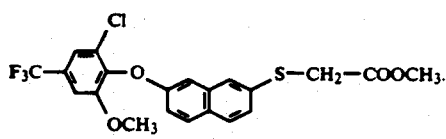

4. A compound according to claim 1, wherein such compound is methyl α-(7-(2-chloro-6-methoxy-4-trifluoromethyl-phenoxy)-naphthalen-2-yl-oxy)-acetate of the formula

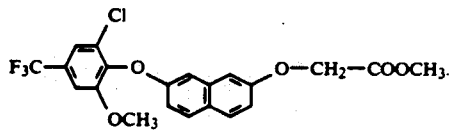

5. A compound according to claim 1, wherein such compound is methyl (R)-α-(7-(2-chloro-6-methoxy-4-trifluoromethyl-phenoxy)-naphthalen-2-yl-oxy)-propionate of the formula

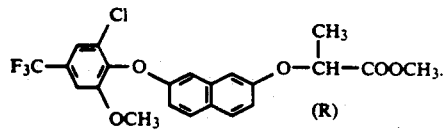

6. A herbicidal composition comprising a herbicidally effective amount of an aryloxynaphthalene compound according to claim 1 and a diluent.

7. A method for combating undesired vegetation, comprising applying to such vegetation, or to a locus from which it is desired to exclude such vegetation, a herbicidally effective amount of an aryloxynaphthalene according to claim 1.

8. The method according to claim 7, wherein the herbicidal compound is an aryloxynaphthalene selected from the group consisting of
methyl α-(7-(2-chloro-6-methoxy-4-trifluoromethyl-phenoxy)-naphthalen-2-yl-thio)-acetate,
methyl α-(7-(2-chloro-6-methoxy-4-trifluoromethyl-phenoxy)-naphthalen-2-yl-oxy)-acetate and
methyl (R)-α-(7-(2-chloro-6-methoxy-4-trifluoromethyl-phenoxy)-naphthalen-2-yl-oxy)-propionate.

9. An aryloxynaphthalene of the formula

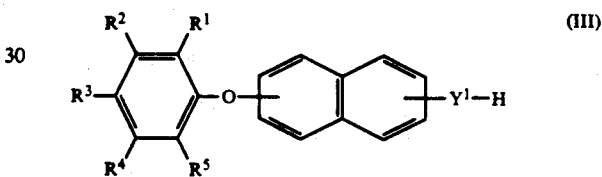

wherein
R¹ is chlorine or fluorine,
R² is hydrogen,
R³ trifluoromethyl or chlorine,
R⁴ is hydrogen,
R⁵ is alkoxy or alkylthio, and
Y' represents oxygen or sulfur.

* * * * *